United States Patent  
Yin et al.

(10) Patent No.: US 9,206,396 B2
(45) Date of Patent: Dec. 8, 2015

(54) METHODS AND DEVICES FOR QUANTITATIVE VIRAL ASSAYS

(75) Inventors: John Yin, Madison, WI (US); Ying Shu, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 11/560,714

(22) Filed: Nov. 16, 2006

(65) Prior Publication Data

US 2007/0111296 A1   May 17, 2007

Related U.S. Application Data

(60) Provisional application No. 60/736,843, filed on Nov. 16, 2005.

(51) Int. Cl.
*C12Q 1/70* (2006.01)
*C12N 7/00* (2006.01)
*C12N 15/86* (2006.01)
*C12Q 1/00* (2006.01)

(52) U.S. Cl.
CPC . *C12N 7/00* (2013.01); *C12N 15/86* (2013.01); *C12N 2760/16051* (2013.01); *C12N 2760/20211* (2013.01); *C12N 2770/36251* (2013.01); *C12N 2795/14151* (2013.01); *C12Q 1/00* (2013.01); *C12Q 1/70* (2013.01)

(58) Field of Classification Search
None
See application file for complete search history.

(56) References Cited

U.S. PATENT DOCUMENTS

2004/0115838 A1*  6/2004  Quake et al. .............. 436/538

OTHER PUBLICATIONS

Lonsdale, et al. A rapid method for immunotitration of influenza viruses using flow cytometry. Journal of virological methods (Netherlands), Jun. 9, 2003, 110 (1) p. 67-71.*
Appleyard et al., 1971 G. Appleyard, A.J. Hapel and E.A. Boulter, An antigenic difference between intracellular and extracellular rabbitpox virus, J. Gen. Virol. 13 (1971), pp. 9-17.*
Lakshmi, et al. Detection of influenza virus induced DNA damage by Comet assay. Mutation Research 442_1999.53-58.*
Appleyard, et al. (An Antigenic Difference between Intracellular and Extracellular Rabbitpox Virus. J. Gen. Virol. 1971; 13: 9-17.*

(Continued)

*Primary Examiner* — Zachariah Lucas
*Assistant Examiner* — Stuart W Snyder
(74) *Attorney, Agent, or Firm* — Kening Li; Miller Canfield

(57) ABSTRACT

A method for quantifying infectious particles of a virus in a sample comprises providing a layer of host cells of the virus, contacting the layer of host cells with a preparation of the sample, and culturing the cells under conditions wherein the cells are submerged in a thin layer of liquid culture medium, and wherein the virus infects host cells and releases its progeny from said infected host cells, imposing a flow of the liquid medium, wherein the spread of the viral progeny to uninfected host cells is enhanced, culturing the cells under conditions to allow further virus infection and viral gene expression, wherein infected host cells develop an observable indication of viral gene expression, and determining the number of infected host cells, whereby the number of infectious particles of the virus in the sample is quantified. The method may be used for measuring viral growth rate or for screening for antiviral compounds. Also provided are microfluidic devices suitable for the inventive method.

12 Claims, 13 Drawing Sheets

(56) References Cited

OTHER PUBLICATIONS

Uckert, et al. In "Methods in Molecular Medicine", vol. 35: Gene Therapy: Methods and Protocols Edited by: W. Walther and U. Stein © Humana Press, Inc., Totowa, NJ; pp. 275-285.*

Earl, et al. "Preparation of Cell Cultures and Vaccinia Virus Stocks" in Curr. Prot. Prot. Sci., John Wiley & Sons, Inc., 1998; pp. 5.12.1-5.12.12.*

Appleyard, et al. An Antigenic Difference between Intracellular and Extracellular Rabbitpox Virus. J. Gen. Virol. 1971; 13: 9-17.*

Mijnes, et al. Complementation of a gl-deficient feline herpesvirus recombinant by allotopic expression of truncated gl derivatives. J. Gen. Virol. 1999; 80: 1799-1805.*

Breedveld, et al. Shear-induced diffusion and rheology of noncolloidal suspensions: Time scales and particle displacements. J Chem Phys, 2001; 114(13), 5923-5936.*

Muratore, et al. A short-term plaque assay for antiviral drug research on herpes simplex virus type 2. New Microbiol. Jul. 1996;19(3):257-61—Abstract only.*

* cited by examiner

Fixed volume addition for virus loading

Figure 4

Masks for microchannels

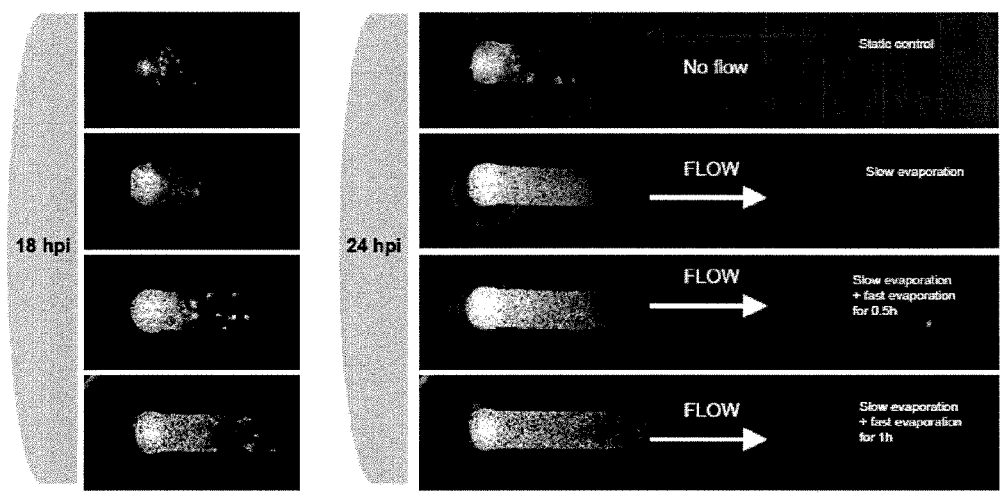
Figure 11
Figure 12
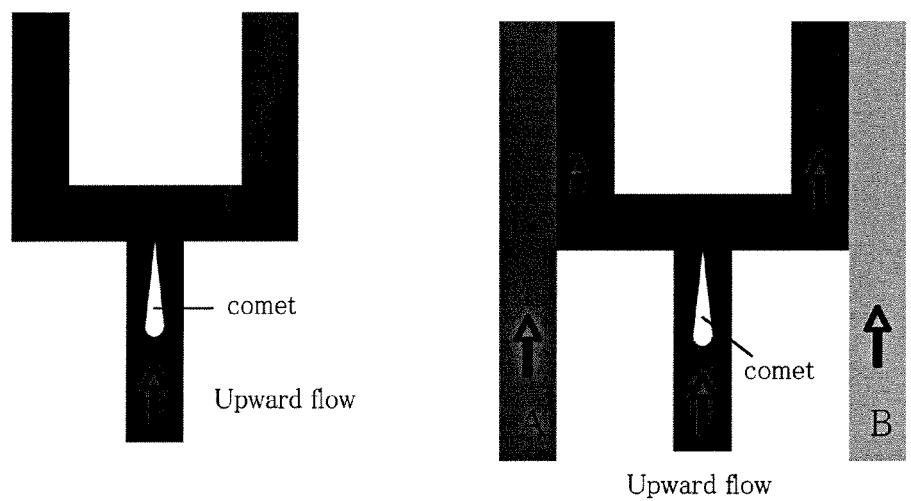

METHODS AND DEVICES FOR QUANTITATIVE VIRAL ASSAYS

CROSS-REFERENCE TO RELATED APPLICATION

This application claims priority of U.S. Provisional Application No. 60/736,843, filed Nov. 16, 2005. The contents of this provisional application is incorporated herein by reference in its entirety.

GOVERNMENT INTEREST

This invention was made with United States government support awarded by the NSF 0331337. The United States has certain rights in this invention.

FIELD OF THE INVENTION

This invention relates to method and microfluidic devices for assaying viral growth, infectivity, and resistance to antiviral substances, and for screening for antiviral compound agents.

BACKGROUND OF THE INVENTION

For many diagnostic and/or treatment purposes, it is highly desirable to be able to measure the number of infectious viral particles in a sample or preparation. For example, rapid and accurate measurement of viral growth is necessary for treatment of viral infections and for monitoring whether a therapeutic strategy is effective in inhibiting viral growth, or whether the virus has developed resistance to compounds used for treatment. Also, as viral vectors are primary delivery vehicles for gene therapy, it is critical that the quantity of the viral particles or dosage in a clinical preparation be rapidly and accurately determined.

Although total particle measurement can be made by techniques such as electron microscopy of viral preparations or measurement of total nucleic acid content, the current "gold standard" for measurement of viral infectivity is the plaque assay. The conventional plaque assay is performed by applying a dilute solution of viruses to a monolayer of susceptible host cells, allowing virus particles to adsorb to cells and then overlaying the cells with a semi-solid agar. Isolated infected cells then produce virus progeny that spread to and infect neighboring cells. Several cycles of virus growth and spread eventually produce a "plaque," a macroscopic island of dying or dead cells surrounded by a sea of uninfected cells. If the initial viral solution is sufficiently dilute, each infectious virus particle in the solution will initiate an infection and cause the formation of one plaque. The total number of plaques thus determines the initial number of infectious particles within the sample. Manual counting of plaques provides the sample infectivity, expressed as a number of plaque forming units (PFU) per unit volume. The size of the plaques also provides a measure of virus infectivity, reflecting the rate and productivity of the virus infections.

This classical plaque assay, however, suffers from the disadvantages that it is time consuming and lacks sufficient sensitivity, in particular because the virus particles released from an infected cell is limited in its ability to spread and reach additional host cells to initiate further rounds of infections.

The instant invention addresses the need for a more accurate method of quantifying infectious viral particles in a population.

If the classical plaque assay is performed with a fluid overlay, instead of an agar overlay, then larger regions of cell death form. These larger regions often have the appearances of comets, as such this modified plaque assay is known as "comet assays." The formation of comets was first reported 35 years ago in studies of vaccinia virus (VV) spread (Appleyard et al., An antigenic difference between intracellular and extracellular rabbitpox virus. *J Gen Virol* 13, 9-17 (1971)), and comet assays have been most widely used in VV research (Payne, Significance of extracellular enveloped virus in the in vitro and in vivo dissemination of vaccinia. *J Gen Virol* 50, 89-100 (1980), Blasco et al., Dissociation of progeny vaccinia virus from the cell membrane is regulated by a viral envelope glycoprotein: effect of a point mutation in the lectin homology domain of the A34R gene. *J Virol* 67, 3319-25 (1993), Katz et al., Identification of second-site mutations that enhance release and spread of vaccinia virus. *J. Virol* 76, 11637-44 (2002); Law et al., Antibody-sensitive and antibody-resistant cell-to-cell spread by vaccinia virus: role of the A33R protein in antibody-resistant spread. *J Gen Virol* 83, 209-22 (2002); Mathew et al., The extracellular domain of vaccinia virus protein B5R affects plaque phenotype, extracellular enveloped virus release, and intracellular actin tail formation. *J Virol* 72, 2429-38 (1998). Vanderplasschen et al., Antibodies against vaccinia virus do not neutralize extracellular enveloped virus but prevent virus release from infected cells and comet formation. *J Gen Virol* 78 (Pt 8), 2041-8 (1997); and Wyatt et al., Highly attenuated smallpox vaccine protects mice with and without immune deficiencies against pathogenic vaccinia virus challenge. *Proc Natl Acad Sci USA* 101, 4590-5 (2004)), and to a more limited extent for herpes simplex virus (Shinkai, Plaque morphology of herpes simplex virus in various cells under liquid overlay as a marker for its type differentiation. *Jpn J Microbiol* 19, 459-62 (1975)), variola virus (Reeves et al., Disabling poxvirus pathogenesis by inhibition of Abl-family tyrosine kinases. *Nat Med* 11, 731-9 (2005)), and influenza virus (Gambaryan et al., Differences in the biological phenotype of low-yielding (L) and high-yielding (H) variants of swine influenza virus A/NJ/11/76 are associated with their different receptor-binding activity. *Virology* 247, 223-31 (1998); Matrosovich et al., Overexpression of the alpha-2,6-sialyltransferase in MDCK cells increases influenza virus sensitivity to neuraminidase inhibitors. *J Virol* 77, 8418-25 (2003)).

SUMMARY OF THE INVENTION

The present invention takes advantage of the discovery that the extent of spread of viral progeny from single infected cells is greater during comet formation than during plaque formation, and that measurement of viral infectivity based on comet formation is faster and more sensitive. Comet size also better reflects virus replicating ability than plaque size. This is because, if a sufficiently high flow exits, each virus particle in the virus 'plume' released by the initial infected cell could in principle find a susceptible host cell, near or far from the virus source, and eventually create an expanse of dead, dying, or detached cells corresponding with the magnitude of the plume (the number of progeny released from the initial infection). By contrast, the plume from an initially infected cell in a traditional plaque assay is confined to the distance to which the virus particles can diffuse. For example, diffusivity in water for VSV particles is about $2 \times 10^{-8}$ cm$^2$/sec (Ware et al., 1973, J. Virol.: 11: 141-145), so over a typical 6-hour VSV infection cycle, the diffusional spread for the viral particles in agar is less than about 0.02 cm, corresponding to an area of $10^{-3}$ cm$^2$, which contains an estimated 300 cells. On the other hand, an initial infected cell typically releases 1000 to 5000 viral progeny, most of which thus will not find an uninfected cell over the time scale of a secondary infection cycle. In short, virus particles originating from the initial infected cell have a better chance in the comet assay, compared to the standard plaque assay, of initiating a secondary infection that will be detected, be quantified, and contribute to further spread. In addition, because the "comets" are more easily observable, a comet based assay is faster than the classical plaque based assays.

The mechanism of comet formation is not known. Their appearance suggests that evaporation and/or convection currents in the fluid medium play a role, however comets also form in apparently stagnant fluid medium in culture wells even in the absence of stirring or swirling. While such convection or evaporation-driven flows in standard six-well culture dishes are simple to implement, they lack precise control over the flow environment, and precise, repeatable and quantitative measurements are difficult.

The present inventors discovered that the flow of medium can be controlled, allowing quantitative analysis of viral infectivity and growth rates, assessment of phenotypic or genetic diversity of individual virus particles released from a single infected cell, as well as quantitative measurements of antiviral activities of compounds. More specifically, methods of the invention control the flow of the media that drives the formation of comets in a micro-fluidic channel.

Accordingly, in one embodiment, the present invention provides a method for quantifying infectious particles of a virus in a sample, the method comprising: 1) providing a layer of host cells of the virus, 2) contacting the layer of host cells with a preparation of the sample, and culturing the cells under conditions wherein the cells are submerged in a thin layer of liquid culture medium, and wherein the virus infects host cells and releases its progeny from said infected host cells, 3) imposing a flow of the liquid medium, wherein the spread of the viral progeny to uninfected host cells is enhanced, 4) culturing the cells under conditions to allow further virus infection and viral gene expression, wherein infected host cells develop an observable indication of viral gene expression, and 5) determining the number of infected host cells, whereby the number of infectious particles of the virus in the sample is quantified.

In a preferred embodiment, the method of the present invention uses the formation of a plaque, preferably a comet shaped plaque, as an indication of viral gene expression. Alternatively, wherein the host cells may be stained with a suitable dye to show viral infection or viral gene expression or a host reaction to the virus infection.

Preferably, digital imaging and computer processing of the images are used to facilitate the quantification of viral growth.

In a preferred embodiment, the layer of host cell is formed on the surface of a cultural medium or a cultural plate.

The method according to the present invention preferably uses a microfluidic device. The microfluidic device preferably comprises a first and a second end reservoir connected by an enclosed channel, wherein the channel has an enclosed bottom surface suitable for host cell adherence and growth, and the end reservoirs are accessible for liquid loading or removal. Further, the layer of host cells is formed on the bottom of surface of the microfluidic device, and the liquid culture medium is controlled to flow from one reservoir to the other reservoir. In a preferred embodiment, the flow is controlled, and the controlled flow of the liquid culture medium is effected by a differential in pressure of the liquid medium in the first and second reservoirs. The liquid culture medium may preferably comprise inert particles so that diffusion of viral particles in the liquid culture medium is enhanced. Preferably, capture by host cells of the viral particles is enhanced.

The present invention further provides a method for measuring growth and spread rate of a virus, the method comprising: 1) providing a layer of host cells of the virus, 2) contacting the layer of host cells with a preparation of the sample, and culturing the cells under conditions wherein the cells are submerged in a thin layer of liquid culture medium, and wherein the virus infects host cells and releases its progeny from said infected host cells, 3) imposing a flow of the liquid medium, wherein the spread of the viral progeny to uninfected host cells is enhanced, 4) culturing the cells under conditions to allow further virus infection and viral gene expression, wherein infected host cells develop an observable indication of viral gene expression, and 5) measuring the observable indication in relation to time.

In a further embodiment, the present invention provides a method for determining antiviral activity of a compound against a virus, comprising: 1) measuring growth rate of the virus in the presence and in the absence of a candidate compound, and 2) comparing the growth rate of the virus in the presence to the growth rate in the absence of the candidate compound, wherein a decrease in the viral growth rate in the presence of the candidate compound indicates that the candidate compound has antiviral activity against the virus.

The present invention in another embodiment also provides a microfluidic device which comprises a first and a second end reservoir connected by an enclosed channel, wherein the channel has an enclosed bottom surface suitable for host cell adherence and growth, and the end reservoirs are accessible for liquid loading or removal. Preferably, the end reservoirs are suitable for storing different amounts of liquid. The microfluidic device according to the present invention are used in such a way that the enclosed channel and the end reservoirs are filled with a liquid, and the end reservoirs contain the liquid in different volumes, and a flow occurs in the channel due to the evaporation of liquids in the end reservoirs. Alternatively, the microfluidic device according to the present invention comprises a source reservoir at one end of the channel, and a sink reservoir at the other end of the channel. When the source reservoir contains an excess amount of liquid in comparison to the sink reservoir, evaporation from the sink reservoir causes flow of the liquid in the channel towards the sink reservoir.

The microfluidic device of the invention may comprise a plurality of microfluidic channels, which may be Y-shaped or branched, so that the flow of the liquid medium from the upstream can be diverted into two channels downstream which may contain different compounds to be tested. These plurality of channels are linked by at least one cross channel.

BRIEF DESCRIPTION OF THE DRAWINGS

Other objects, advantages and novel features of the present invention will become apparent from the following detailed description when considered in conjunction with the accompanying drawings.

FIG. 4 illustrates fixed volume addition of the present invention. A specified volume of fluid is added to Input 2. Because the location where the fluid front ceases to advance depends directly on the volume added, viral infection is localized to the upstream portion of the microchannel.

FIG. 11 shows enhancement of virus spread in the presence of microchannel flow.

FIG. 12 shows potential application of 2-D flow, where virus from a single comet feeds two down-stream channels. Exposure of those down-stream channels to different environmental conditions (e.g., drugs) enables testing of drug conditions on viruses descended from the same infected cell, which should be relatively homogeneous.

DESCRIPTION OF PREFERRED EMBODIMENTS

Figure 6:
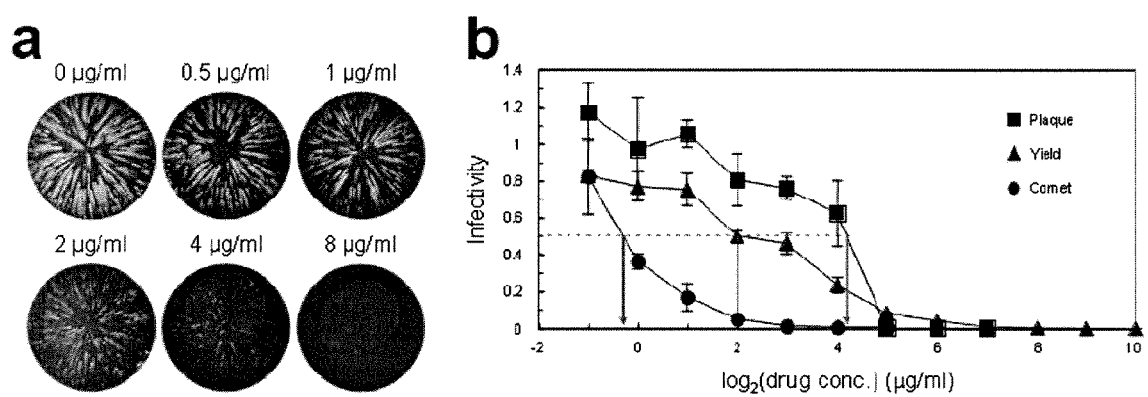
FIG. 6 shows that comet assay measures drug susceptibility with high sensitivity. (a) Dose-dependent inhibition of VSV comet formation by 5-fluorouracil (5-FU). (b) Comparison of virus susceptibility measured by comet, yield and plaque assays. Assays were carried out in triplicate. Grey arrows indicate IC50 values of 1, 4 and 16 μg/ml for comet, yield and plaque assays, respectively.

As described above, the present inventors discovered that the flow of medium can be controlled, allowing quantitative analysis of viral infectivity and growth rates, assessment of phenotypic or genetic diversity of individual virus particles released from a single infected cell, as well as quantitative measurements of antiviral activities of compounds. More specifically, methods of the invention control the flow of the media that drives the formation of comets in a micro-fluidic channel. The methods of the present invention can be adapted for automation and digital imaging, and flow-combined with imaging enables more quantitative measures of infectivity (see e.g. FIG. 6).

In one embodiment, the present invention provides a method for quantifying the number of infectious viral particles in a sample, the method comprising 1) providing a layer of host cells of the virus, 2) contacting the layer of host cells with a preparation of the sample, and culturing the cells under conditions wherein the cells are submerged in a thin layer of liquid culture medium, and wherein the virus infects host cells and releases its progeny from said infected host cells, 3) imposing a controlled flow of the liquid medium, wherein the spread of the viral progeny to uninfected host cells is enhanced, 4) culturing the cells under conditions to allow further virus infection and viral gene expression, wherein infected host cells develop an observable indication of viral gene expression, and 5) determining the number of infected host cells, whereby the number of infectious particles of the virus in the sample is quantified.

Preferably, the layer of susceptible host cells provided in step (1) above is confluent or near-confluent. The layer of host cells is preferably formed on the surface of a cultural medium or a suitable surface of a device such as a cultural plate or a microfluidic device described hereinbelow.

Preferably, the controlled flow is unidirectional. Alternatively, two-dimensional flows (2D flows) are used. For example, a Y-shaped channel is used, where an infected cell in the base of the "Y" is put under flow that splits, resulting in one-comet feeding two flow channels. Each of the resulting two flow channels could also be fed by different streams containing, for example drug A and drug B, see e.g. FIG. 12. This offers several advantages. For example, since the comet is initiated by a single virus particle, viruses descended from the comet are more likely to be genetically homogeneous than viruses from different comets. Hence, the Y-split would allow one to test different environmental conditions (e.g., antiviral drugs, anti-serum, cytokines, competitor virus strains) on virus samples that were genetically identical or near identical.

The observable indication may be a plaque exhibited by host cell death, or cells in a dying process or detachment. In the case of cell death, this may be visible as rounding and lifting of cells adsorbed to the culture surface associated, for example, with disruption of the cytoskeleton (J Virol. 1990 64(4):1716-25. Role of matrix protein in cytopathogenesis of vesicular stomatitis virus. Blondel et al) blebbing of the cell membrane in the case of infection-coupled programmed cell death or apoptosis (J Virol. 1997 February; 71(2):1530-7. Role of early and late replication events in induction of apoptosis by baculoviruses. LaCount and Friesen). The observable indication may also be another observable phenotype of a viral gene expression, for example a viral protein expression which can be detected following a suitable staining procedure with a suitable antibody, for example (Duca K A, et al, Quantifying viral propagation in vitro: toward a method for characterization of complex phenotypes. Biotechnol Prog. 2001 November-December; 17(6):1156-65.)

The observable indication may also be a host cell reaction to the virus infection. Virus infections can activate cellular defensive responses such as interferon (IFN) pathways. Reporters that are linked to infection-mediated activation of such responses then report host cell reactions to virus infection. For example, interferon-responsive host cell promoters (ISREs, interferon-stimulated responsive elements) can be linked to reporters such that Sendai virus infections can activate IFN expression that then drives reporter expression (Ning S, et al, Regulation of the transcriptional activity of the IRF7 promoter by a pathway independent of interferon signaling. J Biol Chem. 2005 Apr. 1; 280(13):12262-70.)

The observable indication may further be the expression of a transgene, such as a gene encoding a fluorescent protein whose expression can be easily monitored or quantified. For example, the host cell may be modified to carry a reporter enzyme whose expression is driven by a virus-inducible promoter (Wang, et al, A cell line that secretes inducibly a reporter protein for monitoring herpes simplex virus infection and drug susceptibility. Journal of Med Virol. 2002 December; 68(4):599-605).

Preferably, the observable indication of viral growth may be digitally imaged and computerized for automated quantification. For example, montage images of infected cells can be collected using established imaging methods (Duca, et al 2001; Endler, et al 2003; Lam, et al 2005; Zhu and Yin, 2006, A quantitative comet assay: imaging and analysis of virus plaques formed with a liquid overlay. Journal of Virological Methods, in press). Digital imaging can be employed to measure signal intensities as a function of position, filter noise, establish signal thresholds, and calculate boundaries of infection at the boundary between detectable and non-detectable signal. Areas of bounded signal may then be quantified.

The present invention further provides a microfluidic device to be used for the above method. The microfluidic device of the present invention in one embodiment comprises a first and a second end reservoir connected by a channel, wherein the channel has a bottom surface suitable for host cell adherence and growth. Preferably, the channel is enclosed such that evaporation is minimized, and the end reservoirs, also referred to as access ports are accessible for liquid loading or removal. The layer of host cells is formed on the bottom of the microfluidic device, and the liquid culture medium is controlled to flow from one reservoir to the other reservoir. The end reservoirs are preferably suitable for storing different amounts of liquid.

Figure 1:
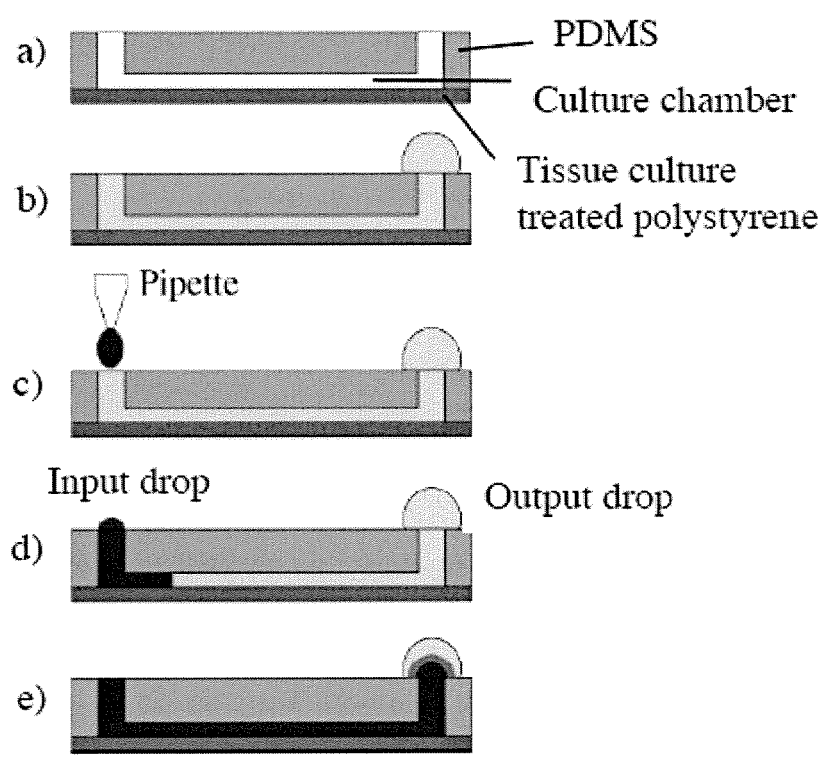
FIG. 1 illustrates passive pumping in a microchannel. (a) A one-input/one output microchannel. (b) The channel is initially filled with fluid (typically via vacuum assisted filling to ensure complete and bubble free filling) and a reservoir drop is placed at the output port. (c) A smaller input drop is dispensed at the input port. (d-e) The difference in curvature between the two drops (input and output) of different volume causes a pressure gradient from the small to the large. Droplet pumping (c-e) occurs. The process can be repeated as necessary with the same or different input solutions.

When the enclosed channel and the end reservoirs are filled with a liquid, and the end reservoirs contain the liquid in different volumes, a flow is induced via surface tension-based passive pumping as described and illustrated in FIG. 1. The pressure p (above atmospheric pressure) inside a drop of fluid is inversely proportional to its radius of curvature R and is given by the Young-Laplace equation:

$$p = \gamma \frac{2}{R}$$

where $\gamma$ is the surface tension of the liquid and R is the radius of the drop. Thus, for a micro-fluidic channel with one reservoir or access port on each end, when a drop is placed at each its ports, and one drop is significantly larger than the other drop, the pressure inside the smaller droplet (high curvature) is higher than that inside the larger one (low curvature). This pressure differential induces pumping flow of fluids going from the smaller drop to the larger drop, until the former is completely depleted or consumed. This is termed passive pumping, the smaller droplet being referred to as the input drop, and the larger drop as the output drop (see e.g. Walker and Beebe, A passive pumping method for microfluidic devices. Lab Chip 2002; 2: 131-134).

The microchannel may preferably be constructed from a hydrophobic material or a material with a hydrophobic surface.

Although for simplicity, FIG. 1 shows only a microchannel with only one input and one output, multiple input/output channel networks are also within the scope of the present invention, and may be important for advanced functions such as localized initiation of virus infections.

Such an approach eliminates the need for multiple input/output connections and their associated dead-volumes and avoids the complexity of systems with integrated active components. Such systems include, for example, microfluidic devices containing on-off valves, switching valves, and pumps. (Unger M A, et al, Monolithic microfabricated valves and pumps by multilayer soft lithography. Science. 2000; 288(5463):113-6; Sin et al, A self-priming microfluidic diaphragm pump capable of recirculation fabricated by combining soft lithography and traditional machining. Biotechnol Bioeng. 2004 Feb. 5; 85(3):359-63.)

The resulting flow may be used to seed cells, change culture media and perform staining within the closed microculture chambers. The present invention controls this flow during the comet formation process. The flow rate U, produced by passive pumping, is determined by the pressure differential between the input and output drops, $\Delta p$, and the fluidic resistance Z of the channel:

$$U = \Delta p Z.$$

Figure 2:
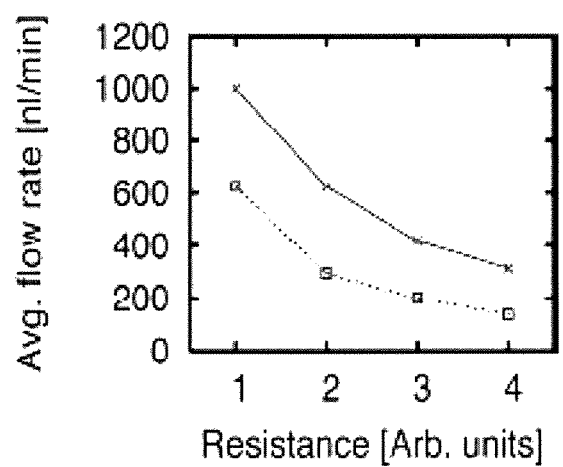
FIG. 2 shows the effects of channel resistance on flow rate. Average flow rate for a 5 μl (crosses), and 10 μl (squares) input drop as a function of channel resistance. The channels all had the same cross-section, but different length, which is linearly related to resistance.

For a given output drop volume, passive pumping flow rate is determined by the input drop volume and the channel resistance. To produce slow flow, a large input drop and high channel resistance is needed. FIG. 2 shows the average flow rates for 5 µl and 10 µl input drops as a function of channel resistance. The flow rate was determined by dividing the input drop volume by the time from flow initiation until the input drop was completely consumed.

Since the input drop volume changes as flow proceeds, the flow rate starts out slow and then increases as the drop gets smaller. Therefore, for a significant period of time, the flow rate is much lower than indicated by the average value. To achieve a more uniform flow rate over time, one can extend the flow period such that the duration of the experiment is significantly shorter than the duration of flow, operating in the more linear part of the flow profile. Alternatively, the input drop may be periodically reconstituted to its original volume to achieve a more constant flow rate.

Channel resistance is determined by the dimensions of its cross-section. For example, in a cylindrical tube of radius R, resistance is proportional to $1/R^4$. Therefore, putting a constriction into a channel can dramatically increase resistance and reduce flow rate, by many orders of magnitude.

Figure 3:
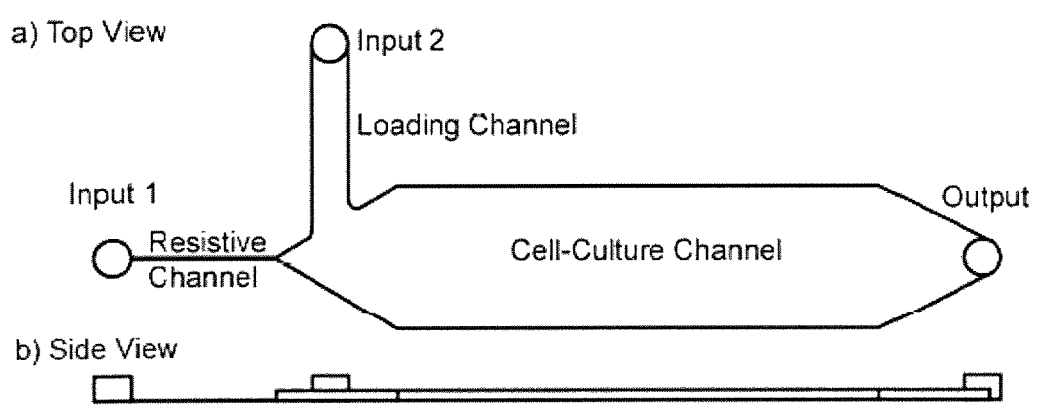
FIG. 3 depicts one design of the micro-fluidic flow channel of the present invention. a) top view, b) side view. The "Resistive Channel" provides resistance to fluid flow from Input 1 to the Output. The side channel or "Loading Channel" is used to introduce the virus to the cells using a fixed volume approach. The Cell-Culture Channel" is generally larger in cross section, and is for monitoring cell infection and spreading of the virus. In one embodiment, the size of the Resistive Channel is H×W×L=10 μm×30 μm×3000 μm), that of the Loading Channel is H×W=200 μm×750 μm, and that of the Cell-culture Channel is H×W=200 μm×3000 μm.

A specific design of the micro-fluidic flow channel of the present invention is shown in FIG. 3 wherein a) is the top view, and b) is the side view. The "Resistive Channel" provides resistance to fluid flow from Input 1 to the Output. The side channel or "Loading Channel" is used to introduce the virus to the cells using a fixed volume approach (see FIG. 4, discussed in more detail below). The Cell-Culture Channel is generally larger in cross section, and may be used for monitoring cell infection and spreading of the virus. In one embodiment, the Resistive Channel has a dimension of 10 µm×30 µm×3000 µm (H×W×L), the Loading Channel of 200 µm×750 µm (H×W), and the Cell-culture Channel of 200 µm×3000 µm (H×W).

One of ordinary skills will recognize that there are many alternative design variables with which to alter the characteristics of the slow-flow. These variables include but are not limited to resistive channel height and width, cell-culture channel height and width, input droplet volume, differences between input and outlet droplet volumes, channel lengths, and input volume-addition time-interval.

Figure 4:
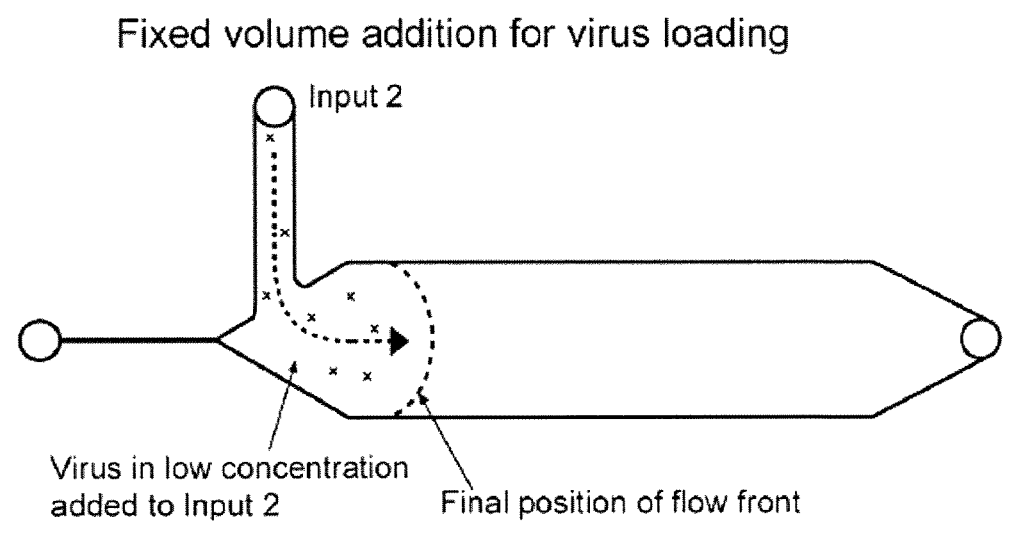

FIG. 4 illustrates a process where a predetermined volume of fluid containing the virus particles is loaded into the device depicted in FIG. 3. Cells may first be seeded into the channel through Input 2. Passive-pumping or direct injection of cells from Input 2 to the Output will fill the Cell-Culture Channel with cells. Following cell addition, a fixed volume of fluid containing a low concentration of virus will be added to Input 2. The volume of virus fluid to be added is controlled or fixed, and is such that the flow front will travel only a small distance into the channel, thereby localizing the infection to cells at the upstream end of the Cell-Culture Channel. After infection, slow flow will be induced by adding a passive-pumping droplet to Input 1, allowing comet formation under controlled flow conditions. Depending on flow rates and assay duration, the droplet size at Input 1 can be maintained by periodic additions to replace lost volume.

The microfluidic device of the present invention takes advantage of the basic concepts described above and can achieve very slow flow rates. For example, the infection assay described below in the Examples uses a flow velocity on the order of 140 μm/h.

As an example, if the Input 1 droplet volume is 8 μL, the Output droplet volume is set at 12 μL, the approximate time-average velocity in the Cell-Culture Channel will be about 113 μm/h and can be maintained for ~4-6 hours after which the droplet volume at Input 1 would drop to ~5 μL, at which point a 3 μL drop could be added to Input 1 and removed from the Output to bring the droplets back to their original volumes and commence slow-flow for another 4-6 hours if necessary.

The task of repeated fluid additions and aspirations can be easily automated using liquid handling automation equipment, well-known and readily available to those skilled in the art. Current commercially available liquid transfer robots such as the Biomek FX allows for precise pipetting in diverse assay plate formats. Automated or semiautomated protocols can be readily adapted to serve a diversity of culture needs or conditions. For examples, see Menzel R. A microtiter plate-based system for the semiautomated growth and assay of bacterial cells for beta-galactosidase activity. Anal Biochem. 1989 Aug. 15; 181(1):40-50; Stock et al, Robotic nanoliter protein crystallisation at the MRC Laboratory of Molecular Biology. Prog Biophys Mol Biol. 2005 July; 88(3):311-27.

Other micro-channel designs could include or involve many other features or techniques to provide flexibility to the slow-flow assay. Cross-flowing channels could be used to localize infections to a smaller region if necessary. For example, host cells in FIG. 5A could be filled into the channel by initially closing the cross-flow ports (inoculation and waste) and loading cell solution into the "source" port and withdrawing this solution through the 'sink' port. Once cells have been allowed to adhere to the channel, source and sink will be closed or covered while the inoculum and waste ports are opened. Then concentrated virus stock solution could be introduced into the inoculum port and permitted to flow through to the waste port, filling the cross-channel with virus solution. The system would then be incubated to allow sufficient time for localized infections of cells within the areas where the Cell-culture Channel and cross-channel intersect. Unbound virus particles would then be washed out of the cross-channel by virus-free wash buffer or medium that is introduced to flow from the inoculation to waste port. The cross-channel would then be closed off, and flow of media could be introduced in the Cell-culture channel, allowing virus released from the localized infected region to spread by flow downstream.

Cell-Culture Channel regions could be joined along their length to reduce any environmental differences between channels. For example, as shown in FIG. 12, flowing feed conditions that enter at the based of the Y-channel and flow upward would split into two streams in the upper half of the Y-channel. Each feature of the microchannel can be scaled as desired. For example, the length of the Cell-Culture Channel could be scaled up to allow for many Loading Channels to exist along its length, allowing for multiple cell types and viruses to be tested in the same environment.

Figure 5A:
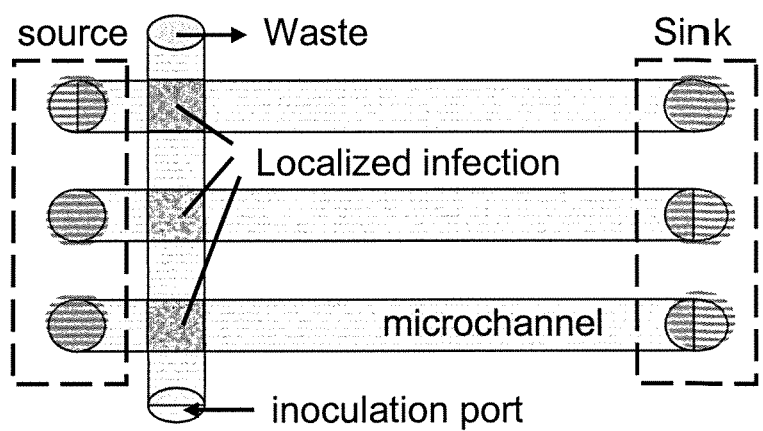
FIG. 5A illustrates a multi-channel design of the microfluidic device of the present invention with an intersecting loading channel.

FIG. 5 depicts one embodiment of microfluidic device of the present invention where a plurality of channels loaded with host cells intersect, preferably perpendicularly, with a channel for viral loading. This design is suitable for testing or screening multiple candidate anti-viral compounds simultaneously. For example, the culture of cells in the channel and initiation of localized infections and channel washes would be carried out as described in the previous paragraph. Then test solutions containing, for example, different drugs or different concentrations of the same drug would be flowed through each channel. The channel intersections are generally closable. For example, if the channels are filled with liquid, one may use passive pumping to inoculate the channel intersections with virus. This would be implemented by placing a large liquid droplet of buffer or medium at the "waste" port of FIG. 6A and a smaller liquid droplet containing virus stock at the "inoculation port." Owing to the larger pressure differential between the inoculation and waste ports than between the inoculation and other ports, virus stock solution will then flow through the cross-channel without significantly flowing into the Cell-culture channels. In an alternative embodiment one can close ports to the environment to prevent flows in or out of a channel. Reversible port closing is easily done by placing a flat block of PDMS or other material over the port. Here one could close 'source' and 'sink' ports in FIG. 5A, and by active pumping introduce an inoculation solution containing virus to the 'inoculation port.' In the absence of a block to the 'waste' port, inoculation solution should then flow through the cross-channel from inoculation port to waste, enabling as before the localized infection of cells.

Figure 5B:
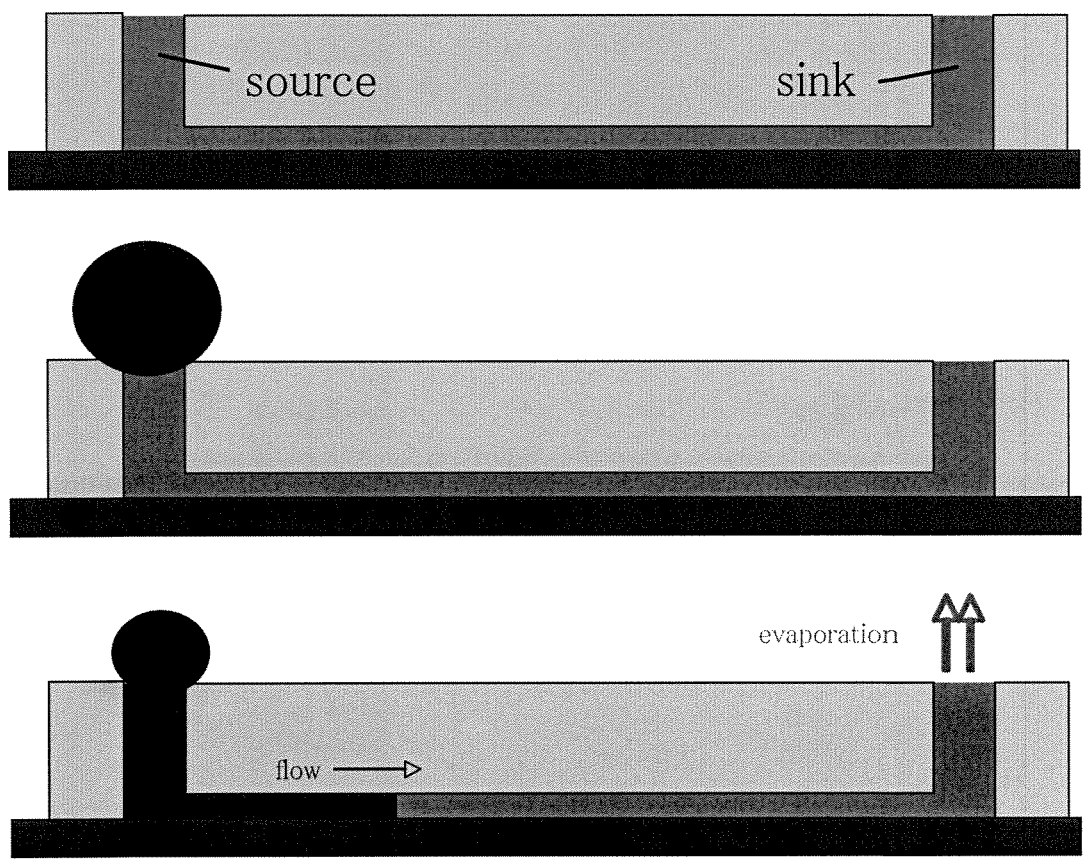
FIG. 5B shows a methodology for evaporation-driven flows where evaporation of liquid from the sink reservoir drives flow of liquid from the droplet in the source reservoir through the channel.

In a preferred embodiment, the end reservoirs are exposed to the environment or otherwise positioned to allow evaporation of the fluid medium. Such an evaporation-driven method of passive pumping may achieve a lower flow rate sometimes desirable. Initially the channels as well as source and sink reservoirs are filled to capacity (FIG. 5B). Then a droplet of water is added to the source reservoir. Over time water that leaves the sink by evaporation drives the flow of water from the source droplet into the channel so the flow rate within the channel matches the evaporation rate from the sink reservoir. Although evaporation also will occur from the source droplet, so long as the amount of water evaporation is small relative to the droplet size, evaporation from the droplet should have negligible effect on the flow within the channel. This was the method used to drive flow in the demonstration of flow-enhanced infection spread in microchannels (see FIG. 11).

Figure 5C:
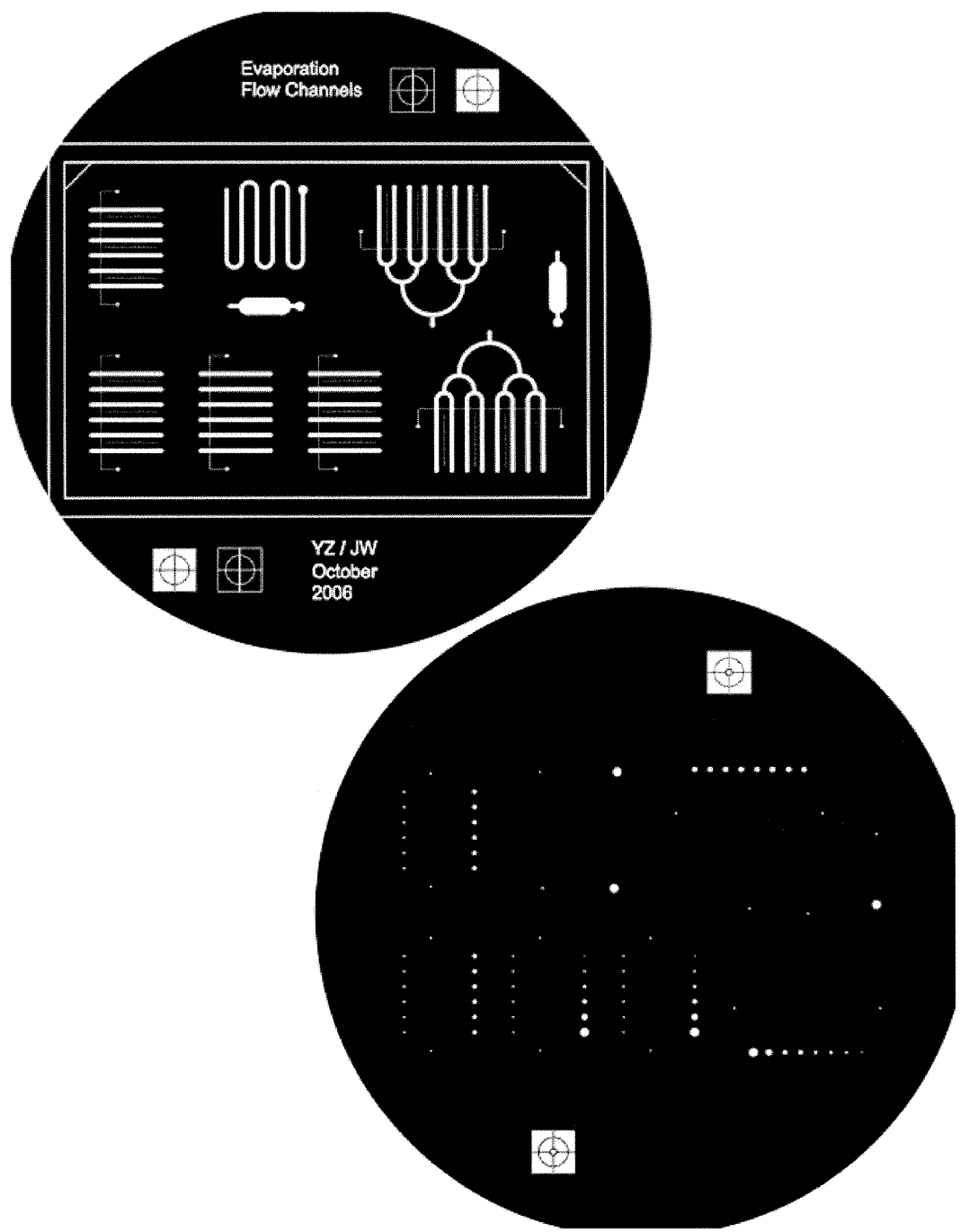
FIG. 5C shows two masks used to fabricate master pattern for microchannels. The masks allow spatial control of exposure of polymer to UV light in the photolithographic process used to create 3-D master molds, which later also serve as molds to create PDMS channels.

FIG. 5C provides examples of preliminary masks used to create the master pattern for microfluidic channels. The two masks allow for two-layer patterns with channels defined by the lower layer and reservoirs to channels defined in the second layer.

In another embodiment, the liquid culture medium may further comprise a suitable amount of inert particles such that diffusion of viral particles in the liquid culture medium is enhanced. For example, Poly(methyl methacrylate) or PMMA can be synthesized and sieved to produce 90±15 micron diameter particles that in the presence of fluid shear can enhance diffusion (Breedveld, et al, Shear-induced diffusion and rheology of noncolloidal suspensions: Time scales and particle displacements. J Chem Phys, 114(13), 5923, 2001). It is known that effective diffusion rate of a solute (including virus particle or macromolecule) in a flowing suspension with added inert particles (or droplets) is higher than in a fluid without added particles (see e.g. Zydney and Colton. Augmented solute transport in the shear flow of a concentrated suspension. Physicochem. Hydrodyn., 10:77-96, 1988). Interactions between the added particles creates or enhances fluctuations in the particle-fluid interactions that are analogous to Brownian (thermal) motion. Such enhancements to virus mobility would further enhance the adhesion of the released virus particles to the host cell.

It is also preferable that the dilution effects be minimized, that is, by minimizing the volume of liquid above the cell monolayer.

The method of the invention for measuring growth rate of a virus may be used for measuring the observable indication in relation to time. For example, one may consider the growth and spread dynamics of a recombinant virus that encodes a fluorescent protein such as green fluorescent protein, whose increasing expression (and detectability) correlates with the development within the cell of virus progeny. Essentially, infected cells are detectable based on their expression of fluorescent protein. Then virus produced and released by a single infected cell may trigger secondary infections in many cells that are down-stream of the initial infected cell. The observable will be a comet of detectable fluorescence whose head is initially bright, followed by an ever lengthening tail. How the shape and size of this pattern changes over time will reflect characteristics of the virus growth rate. High growth rates will correlate with large numbers of virus progeny produced in short times, producing rapid growing comets. If one wishes to perform the same kind of characterization for non-recombinant viruses, then one may immunocytochemically label different comets at different stages of development, providing a population-averaged measure of growth rate.

The method of the invention for measuring growth rate of a virus may be used for determining antiviral activity of a compound, whereby the viral growth rate is measured in the presence of a candidate compound, which growth rate is compared to a suitable control where the candidate compound is absent, wherein a decreased growth rate in the presence of the candidate compound indicates that the compound has antiviral activity.

Any plaque forming viruses are suitable for use with the method and devices of the present invention, such as influenza viruses, HIV-1, vaccinia, and herpes viruses, and variola virus (small pox). Additional plaque-forming natural or recombinant viruses include, for example, west nile virus, dengue virus, herpes simplex virus, human cytomegalovirus, varicella-zoster virus, ebola virus, coronavirus (including SARS virus), Venezuelan equine encephalitis virus, and western equine encephalomyelitis virus.

Digital imaging and analysis of the comets could improve the sensitivity of drug susceptibility assays. The image of the comet may be captured digitally using commercially available equipment, which is then processed to calculate viral infectivity.

The following examples are intended to illustrate preferred embodiments of the invention and should not be interpreted to limit the scope of the invention as defined in the claims.

EXAMPLES

Example 1

Comet Assay Measures Drug Susceptibility with High Sensitivity

1. Methods

Cell Culture.

Baby hamster kidney (BHK-21) cells were originally obtained from Dr. I. Novella (Medical College of Ohio) and grown as monolayers at 37° C. in a humidified atmosphere containing 5% $CO_2$. Growth medium consisted of Minimum Essential Medium Eagle with Earle's Salts (MEM, Cellgro), 10% fetal bovine serum (FBS, Hyclone), and 2 mM Glutamax I (Glu, Gibco). Cells were subcultured approximately every fourth day. For subculture, monolayers were rinsed with Hank's Balanced Salt Solution (HBSS, Hyclone), incubated in 0.05% trypsin/0.53 mM EDTA (Gibco) for 5 minutes, and replated in fresh growth medium at a 1:30 dilution. No antibiotics were used and cells were subcultured no more than 100 passages to minimize the artifacts due to cell senescence. Viability of cell populations, as determined by trypan blue exclusion, at the time of experiments always approached 100%. In all the antiviral assays used in this paper, BHK cells were plated at a density of $5\times10^5$ cells/well in 6-well culture plates one day before infection.

Plaque Assays.

Serial 10-fold dilutions of recombinant VSV that expresses green fluorescence protein (rVSV-GFP), generously provided by Michael Whitt, were made in infection medium consisting of MEM, 2% FBS and 2 mM Glu. Monolayers were infected with 200 μl of virus suspension and incubated for one hour with gentle rocking every 20 minutes to keep the monolayers moist and to distribute the virus evenly. Then the inoculum was removed. The monolayers were rinsed with HBSS and overlaid with 2 ml of 0.6% agar (w/v). For the overlay, agar noble (Becton Dickinson) was hydrated with ultrapure water (deionized water, >18.2 mΩ·cm resistivity, 10% of the desired final volume) and sterilized by autoclaving at 121° C. for 10 minutes. The sterile agar solution was combined with infection medium at 42° C. to make the overlay mixture. The plates were incubated at 37° C. for approximately 20 hours and then fixed with PFA solution consisting of 4% paraformaldehyde (w/v) and 5% sucrose (w/v) in 10 mM phosphate buffered saline (PBS, Sigma). After 3 hours, the agar overlay was removed and the monolayers were rinsed twice with PBS and stained with 0.1% crystal violet in 20% ethanol to visualize plaques. Virus infectivity titers were expressed as plaque forming unit (PFU) per ml.

Comet Assays.

BHK cells were infected with 200 μl of serial 10-fold dilutions of rVSV-GFP. After 1 hour of adsorption, the inoculum was removed. The monolayers were rinsed with HBSS and overlaid with 3 ml of infection medium. The plates were incubated at 37° C. and then fixed with PFA solution at indicated time. After 30 min, the monolayers were rinsed with PBS and stained with crystal violet. As control samples, infected cell monolayers overlaid with 3 ml of 0.6% agar were fixed at the same time and then stained with crystal violet.

Immunocytochemistry.

VSV-mediated expression of GFP was too faint to detect before 16 hours post-infection (HPI), so instead we visualized the distribution of VSV-glycoprotein (VSVG) by indirect immunofluorescence. Rinse solution, pre-block solution and block solution was made before staining. Rinse solution consisted of PBS and 0.1% saponin (Sigma). Pre-block solution consisted of PBS, 0.1% saponin and 5% natal calf serum (NCS, Hyclone). Block solution consisted of PBS, 0.1% saponin, 5% NCS and 0.2% bovine serum albumin (BSA, Jackson Immunoresearch). After fixation, the agar overlay was removed and the plates were stored in PBS at 4° C. When ready to staining, monolayers were washed once with 1 ml of rinse solution and once with 1 ml of pre-block solution; each wash lasted 10 minutes. Cells were then washed for 20 minutes with 1 ml of block solution to minimize the nonspecific binding. A monoclonal antibody against VSV-G (V5507, Sigma) was diluted 1:1000 in pre-block solution and 0.5 ml of the primary antibody was added to each well. After 1 hour of incubation, cells were washed with rinse solution, pre-block solution and block solution as before. A Cy3-conjugated affinipure F(ab')$_2$ fragment donkey anti-mouse antibody (Jackson Immunoresearch) was diluted 1:300 in pre-block solution. Monolayers were overlaid for 1 hour in 0.5 ml of secondary antibody. After incubation, cells were washed twice with rinse solution to remove unbound antibody. Plates were stored in PBS at 4° C. before imaging. During the whole process, the plates were covered with foil and put on a rotator at room temperature.

Particle Tracking.

Red fluorescent microspheres 1.0 μm in diameter (Molecular Probes) were used as tracers to demonstrate the radial movement of flows in six-well culture plates (Costar). The particles were diluted to a mass fraction of $10_{-5}$ (high concentration solution) or $10_{-7}$ (low concentration solution) in with ultrapure water. The location of the particles was identified at 4× magnification by a Nikon Eclipse TE300 inverted epifluorescent microscope equipped with a Prior XYZ translation stage. A monochrome SensSys 4.0 cooled CCD camera driven by MetaMorph 4.0 software (Universal Imaging) running on a Pentium II (Windows NT 4.0) captured digital images of the particles. High concentration solution was used and images were acquired every eight hours for two days. The images were analyzed by a MatLab 7.0 program, calculating intensity of light, for various times from a solution containing fluorescent microspheres vs. the distance away from the vertical wall of a well. Low concentration solution was used and images were acquired every 10 seconds for an hour to track single particle movement. The images were processed by PhotoShop 7.0 (Adobe) to optimize their brightness and contrast. The particle trajectories were mapped and velocities were measured either manually or automatically by using the software developed by Daniel Blair and Eric Dufresne. Solution volume per well and focus plane matched those of our standard comet assay.

Comet-Reduction Assays.

(1) Comet formation. Confluent monolayers of BHK cells in six-well culture plates were inoculated with approximately 500 PFU per well of rVSV-GFP in infection medium. After one hour of adsorption at 37° C., unbound virus was washed away with HBSS and the cells were overlaid with 3 ml of infection medium with 2-fold dilutions of 5-fluorouracil (FU). At 15 HPI, the cell monolayers were fixed and stained as described above. (2) Determination of virus infectivity. A HP ScanJet ADF C6270A flatbed scanner was used to capture the image of each well, which was then processed by Photoshop to optimize its brightness and contrast using the same set of parameters. By setting an appropriate threshold in a MatLab program, we assigned every pixel of each image a value of either 0 or 255, corresponding to regions of noninfected cells (no light transmission) or dead cells (complete light transmission). These values were then used to calculate the virus infectivity, defined here as the ratio of dead cells (area) to total cells. The threshold was determined by measuring pixel values of stained control cell monolayers that showed no signs of cell death in the absence of virus. The threshold was set as ($\mu+3\alpha$), where $\mu$ was the mean pixel value and $\alpha$ was the standard deviation. This choice of the threshold ensures that over 99 percent of the pixel values of our control samples (non-infected cells) would be assigned a value of 0.

Plaque-Reduction Assays.

Monolayers were infected with 200 μl of virus suspension containing approximately 50 to 100 PFU per well. After 1 hour of adsorption at 37° C., the inoculum was removed and the monolayers were overlaid with 3 ml of 0.6% agar (w/v) containing the appropriate concentrations of FU; three wells were used per drug concentration. For the overlay, the sterile agar solution was mixed with 1.1× concentrations of drug in infection medium at 42° C. The following final drug concentrations were used in the assay: 0, 0.5, 1, 2, 4, 8, 16, 32, 64, 128 μg/ml. At 24 HPI, monolayers were fixed and stained, and the plaques were enumerated. By using as reference the number of plaques obtained in the controls (untreated and infected cultures), the drug concentrations required to reduce the number of plaques by 50% ($IC_{50}$) were calculated from the dose-response curves.

Yield-Reduction Assays.

BHK cell monolayers were infected with rVSV-GFP at of multiplicity of infection (MOI) of 1. After one hour of adsorption at 37° C., the unadsorbed virus was removed by washing three times with HBSS; then medium containing a range of concentrations of FU were added; three replicates were used per drug concentration. At 20 HPI, the virus was harvested and titrated by plaque assay. By using as reference virus yield in the controls, the drug concentrations required to reduce the virus yield by 50% ($IC_{50}$) were calculated from the dose response curves.

2. Results

VSV comet assays in the presence of 5-fluorouracil (5-FU), a base analog and known inhibitor of VSV growth showed that the drug inhibited the formation of comets in a dose-dependent manner, reducing both their average width and length at higher drug concentrations (FIG. 6a). Comet spread was visibly reduced for drug concentrations increasing from 0 to 0.5 to 1.0 μg/ml, and comets could no longer be detected at 16 μg/ml (not shown). To quantify these inhibitory effects, a digital scanner was used to capture images of the culture wells, and process the images to optimize their brightness and contrast. A program wasdeveloped to automatically distinguish and quantify regions of viable cells from regions of dead cells. The resulting dose-response curve revealed a smooth, quantitatively reproducible, monotonic decline in virus infectivity with increasing drug levels and a 50 percent inhibition concentration (IC50) of 1 μg/ml (FIG. 6b). For comparison, we also tested the effects of 5-FU on VSV growth by yield and plaque assays. In contrast with the comet assay, neither the yield nor plaque assay exhibited detectible sensitivity to drug below 1.0 μg/ml; further, both retained detectable infection at a drug concentration of 16 μg/ml. Moreover, based on IC50 values, the comet assay was 4- and 16-fold more sensitive than the yield and plaque assays, respectively (FIG. 6b). Further, the comet assay for VSV required only 15 hours of incubation while the yield and plaque assays required 20 and 24 hours of incubation to ensure maximum yields and readily distinguishable visible plaques. Finally, the yield and plaque assays required further manual counting of plaques, which were bypassed with the comet assay.

Example 2

Cells Grow in Microchannels

Microchannels were made from poly(dimethylsiloxane) (PDMS), with a configuration of two ports joined by a channel, as shown in FIG. 1. Typical total volume of the channel and two ports is 8 microliters. The 'floor' of the microchannel is typically the bottom of a culture well in a standard six-well polystyrene culture plate. Cells added to the channel through one port adhere to the 'floor' and eventually flatten out and form a monolayer.

Figure 7:
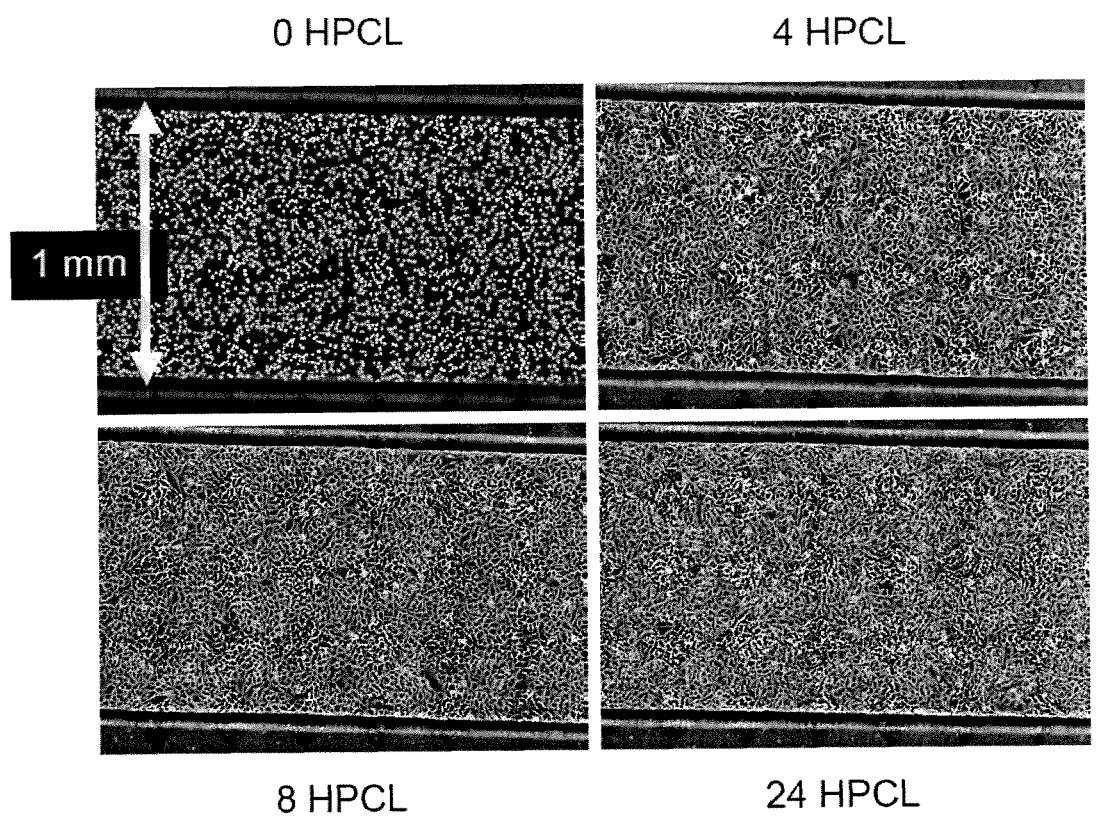
FIG. 7 shows that BHK cells grow in microchannels as a function of time (HPCL=hours post cell loading). Channel is in horizontal orientation, viewed from above.

Baby hamster kidney (BHK21) cells were seeded into microchannels at 1000 cells/mm$_2$, in the presence of growth medium. Phase contrast images were obtained at indicated times (hours post cell loading=HPCL=number of hours after cells were loaded into the microchannel). Representative images are shown in FIG. 7.

Quantification of Cell Growth in Microchannels.

Figure 8:
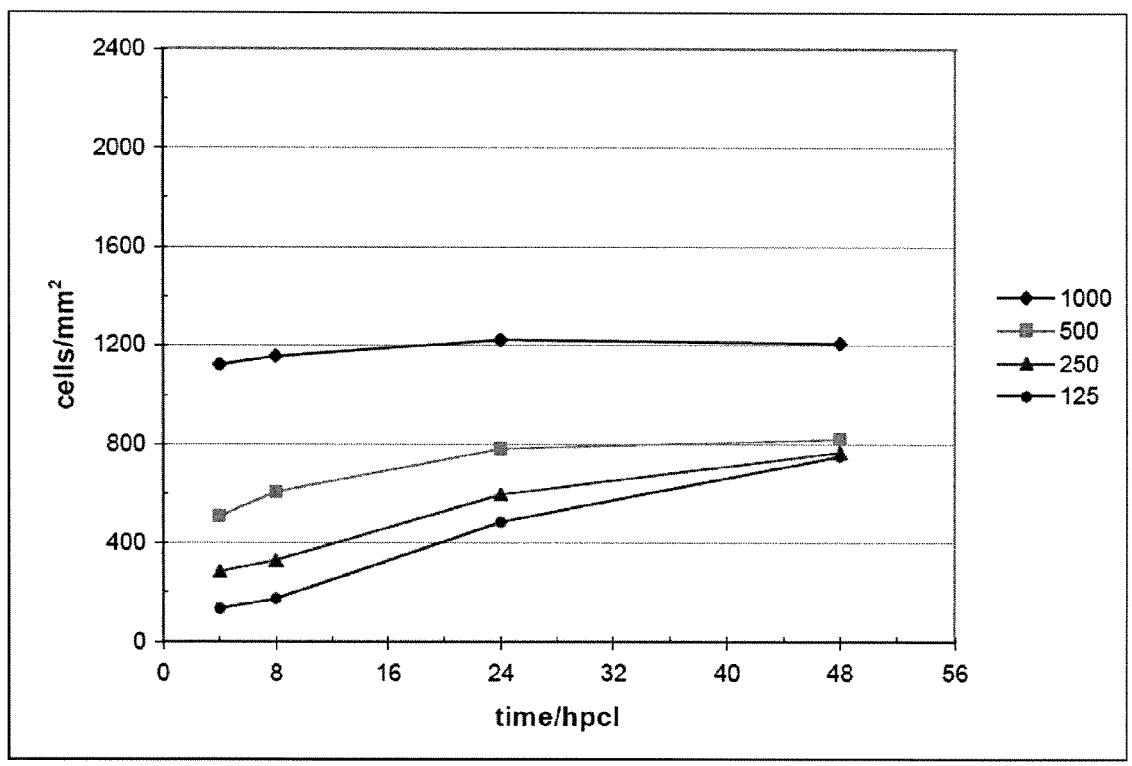
FIG. 8 shows the effects of initial cell loading on dynamics of cell growth in microchannels.

A BHK cell suspension was injected into a channel through one port. Such cell loading was performed with several channels in parallel. At indicated times post cell loading, a PDMS slice was peeled off and cell monolayers were fixed with 4% paraformaldehyde and cell nuclei were stained with DAPI. Fluorescent images were taken at different positions ¼, ²⁄₄, and ¾ down the length of the channel. A program written in MatLab was run to automatically calculate the surface cell density based on the number of nuclei detected in each image. To minimize biases from cell loading effects on cell density, average cell densities were calculated from the densities three positions (negligible differences in cell density were observed at different positions in the channel). Overall results for different initial cell loadings, from 125 to 1000 cells/mm2, are shown in FIG. 8. Observations: (a) all seeded cells increased in area density (number of cells per area) over the 48 hour period, (b) cells seeded at or below 500 cells/mm2 increased up at least 60 percent, to about 800 cells/mm2 over 48 hours, while cells seeded at 1000 cells/mm2 only increased about 20 percent to about 1200 cells/mm$^2$.

Example 3

Cells in Microchannels Are Susceptible to Infection by Virus

Figure 9:
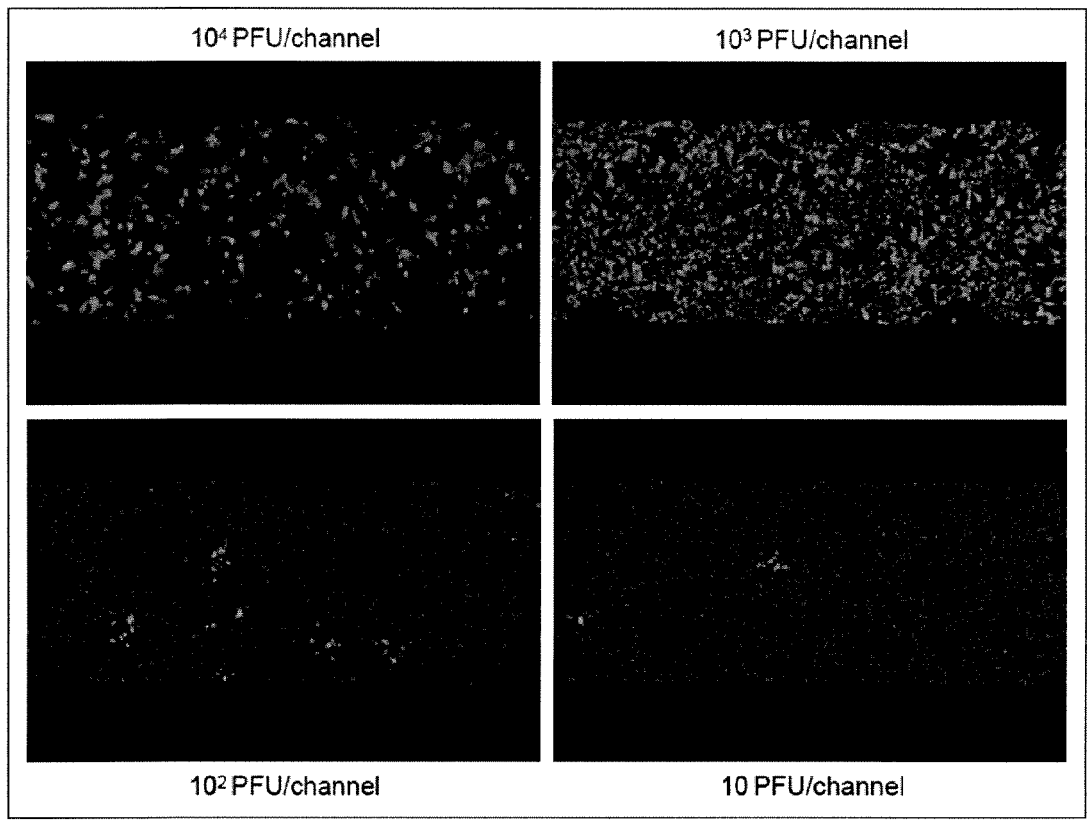
FIG. 9 shows viral infections of cells in microchannels. Spots of light grey are virus protein against the dark grey cell nuclei background. (No color figures are allowed in patent applications, hence grey and dark grey, not red)

BHK cells were loaded into the microchannels at $4 \times 10^6$ cells/ml to create confluent monolayers. Growth medium was removed and vesicular stomatitis virus (rVSV-GFP1) was added. The virus is a recombinant form of VSV that expresses GFP early in the infection cycle; this strain was provided by Prof. Sean Whelan (Harvard Medical School). We seeded virus into channels over three orders of magnitude, from 10 to 10,000 plaque forming units (infectious particles) per channel. Following introduction of the virus into the channels both ports of the channels were covered with PDMS to prevent evaporation, maintaining a static fluid environment. At 15 hours post infection, PDMS slices were peeled off. Cell monolayers were fixed and then stained with Cy3-attached anti-G antibody and DAPI. Fluorescent images of the infected cells were visible based on expression of VSV glycoprotein (red) and cell nuclei (blue), as shown in FIG. 9.

The results show that cells in microchannels are susceptible to infection by virus in a dose-dependent manner, ranging from high multiplicity of infection (MOI), where all cells are simultaneously infected (10,000 PFU per channel) to low MOI, where only a small minority of cells are infected (10 PFU per channel). In addition, virus released by infected cells can spread to and infect nearby cells (apparent at 10 and 100 PFU per channel as clusters of red cells expressing virus G protein).

Example 3

Figure 10:
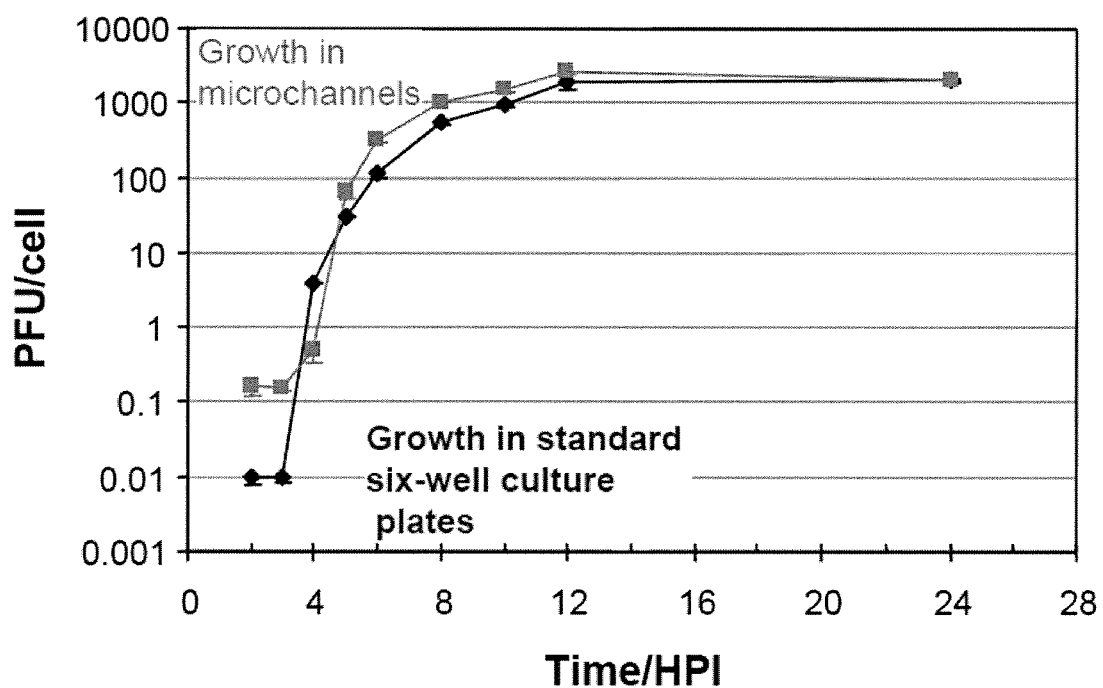
FIG. 10 shows that virus (rVSV-GFP) grows with similar behavior in microchannels and in plates for high MOI (5) infections.

Productivity of Virus Infections in Microchannels is Comparable to Productivity in Standard Culture Wells Synchronized one-step growth cultures of rVSV-GFP1 were performed in microchannels. BHK cells were loaded into the microchannels at $4 \times 10^6$ cells/ml. After the cells adhered to the floor of the channel, growth medium was removed and virus inoculum at multiplicity of infection 5 was injected into the channels. The virus solution was permitted to adsorb to cells and then washed away with hanks balanced salt saline. Then medium containing 2 percent serum was added into the channels. At indicated times post infection, supernatant was taken, frozen and later titered by plaque assay. Data for channels represent values from different channels (1 channel yields one data point). Results are shown in FIG. 10. Comparable productivities per cell were found for one-step growth in channels and standard cultures.

Example 3

Flow-Enhanced Spread of Virus Infections in Microchannels

BHK cells were loaded into the microchannels at $4 \cdot 10^6$ cells/ml to create confluent monolayers. Control and test channels were all inoculated with one microliter of virus inoculum containing fewer than 10 plaque forming units; this one microliter volume is sufficient to displace the initial volume of fluid in the port. Both ports of the control "no-flow" sample were covered with pieces of PDMS to minimize evaporation from the channel and thereby maintain a static fluid environment. The test samples were inoculated in the same manner, but flows were induced by creating imbalances in the evaporation rates from the two ports, as follows. A 5-microliter droplet of 2% medium was added on one port. Therefore, when evaporation occurred, medium flowed from the droplet through the channel to the other port. To achieve slow-flow conditions samples were placed in a 'high-humidity' (or slow evaporation) incubator, containing a pan of water. Fast-flow conditions were achieved by placing samples in a 'low-humidity' (fast evaporation) incubator. Two samples were put in fast-evaporation incubator from 10 HPI for 0.5 or 1 hour and then returned to the slow-evaporation incubator. Images of green fluorescent protein, expressed following infection by rVSV-GFP1, were taken at 18 and 24 HPI respectively, as shown in FIG. 11.

Example 4

Digital Imaging Improves Drug Sensitivity Assays

Confluent monolayers of BHK cells in six-well culture plates were inoculated with approximately 500 PFU per well of rVSV-GFP in an infection medium. After one hour of adsorption at 37° C., unbound virus was washed away with HBSS and the cells were overlaid with 3 ml of infection medium with 2-fold dilutions of 5-fluorouracil (FU). At 15 hours post infection (HPI), the cell monolayers were fixed and stained as described above. A HP ScanJet ADF C6270A flatbed scanner was used to capture the image of each well, which was then processed by Photoshop (Adobe) to optimize its brightness and contrast. By setting an appropriate threshold in a MatLab 7.0 software program every pixel of each image was assigned a value of either 0 or 255, corresponding to regions of noninfected cells (no light transmission) or dead cells (complete light transmission), respectively. These values were then used to calculate the virus infectivity, defined here as the ratio of dead cells (area) to total cells. The threshold was determined by measuring pixel values of stained control cell monolayers that showed no signs of cell death in the absence of virus. The threshold was set as $(\mu+3\alpha)$, where $\mu$ was the mean pixel value and $\alpha$ was the standard deviation. This choice of the threshold ensures that over 99 percent of the pixel values of our control samples (non-infected cells) would be assigned a value of 0.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. Furthermore, the teachings and disclosures of all references cited herein are expressly incorporated in their entirety by reference.

What is claimed is:

1. A method for quantifying infectious particles of a virus in a sample, the method comprising:
    1) providing a layer of host cells of the virus,
    2) contacting the layer of host cells with a preparation of the sample, and culturing the cells under conditions wherein the cells are submerged in a thin layer of liquid culture medium, and wherein the virus infects host cells and releases its progeny from said infected host cells,
    3) imposing a unidirectional or two-dimensional flow of the liquid medium when the cells are being cultured under the thin layer of liquid medium, wherein the spread of the viral progeny to uninfected host cells is enhanced, wherein infected host cells develop an observable indication of viral gene expression which is a comet-shaped plaque, and
    4) observing and quantifying the number of plaques in the layer of host cells thereby determining the number of infected host cells, whereby the number of infectious particles of the virus in the sample is quantified.

2. The method according to claim 1, wherein the host cells are stained with a suitable dye to show viral infection or viral gene expression or a host reaction to the virus infection.

3. The method according to claim 1, wherein the observable indication is digitally imaged and computer processed.

4. The method according to claim 1, wherein the layer of host cell is formed on the surface of a culture medium or a culture plate.

5. The method according to claim 1, wherein a microfluidic device is used,
    wherein the microfluidic device comprising a first and a second end reservoir connected by an enclosed channel, wherein the channel has an enclosed bottom surface suitable for host cell adherence and growth, and the end reservoirs are accessible for liquid loading or removal, and
    wherein the layer of host cells is formed on the bottom of surface of the microfluidic device, and wherein the liquid culture medium is controlled to flow from one reservoir to the other reservoir.

6. The method according to claim 5, wherein the controlled flow of the liquid culture medium is effected by a differential in pressure of the liquid medium in the first and second reservoirs.

7. The method according to claim 5, wherein the liquid culture medium comprises inert particles such that diffusion of viral particles in the liquid culture medium is enhanced.

8. The method according to claim 7, wherein capture by host cells of the viral particles is enhanced.

9. A method for measuring growth rate of a virus, the method comprising:
    1) providing a layer of host cells of the virus,
    2) contacting the layer of host cells with a preparation of the sample, and culturing the cells under conditions wherein the cells are submerged in a thin layer of liquid culture medium, and wherein the virus infects host cells and releases its progeny from said infected host cells,
    3) imposing a flow of the liquid medium, wherein the spread of the viral progeny to uninfected host cells is enhanced,
    4) culturing the cells under conditions to allow further virus infection and viral gene expression, wherein infected host cells develop an observable indication of viral gene expression which is a comet-shaped plaque, and
    5) observing and quantifying the number of plaques in the layer of host cells at more than one time point, thereby determining the number of infected host cells in relation to time.

10. A method for determining antiviral activity of a compound against a virus, comprising: 1) measuring the growth rate of the virus according to claim 9 in the presence and in the absence of a candidate compound, and 2) comparing the growth rate of the virus in the presence to the growth rate in the absence of the candidate compound, wherein a decrease in the viral growth rate in the presence of the candidate compound indicates that the candidate compound has antiviral activity against the virus.

11. The method according to claim 1, wherein the layer of host cells is a monolayer.

12. The method of claim 1, wherein a unidirectional flow of liquid medium is imposed in step 3).

* * * * *

UNITED STATES PATENT AND TRADEMARK OFFICE
CERTIFICATE OF CORRECTION

PATENT NO. : 9,206,396 B2  
APPLICATION NO. : 11/560714  
DATED : December 8, 2015  
INVENTOR(S) : John Yin et al.

Page 1 of 1

It is certified that error appears in the above-identified patent and that said Letters Patent is hereby corrected as shown below:

ON THE TITLE PAGE

(75) Inventor should read: John Yin, Madison, WI (US); Ying Zhu, Madison, WI (US)

Signed and Sealed this  
First Day of March, 2016

Michelle K. Lee  
*Director of the United States Patent and Trademark Office*